United States Patent [19]

Howes

[11] 4,072,146

[45] Feb. 7, 1978

[54] VENOUS CATHETER DEVICE

[76] Inventor: Randolph M. Howes, 1529 McElderry St., Baltimore, Md. 21205

[21] Appl. No.: 721,215

[22] Filed: Sept. 8, 1976

[51] Int. Cl.² .................... A61B 5/02; A61M 25/00
[52] U.S. Cl. .................... 128/2.05 D; 128/2.05 F; 128/214.4; 128/348
[58] Field of Search .......... 128/2 M, 2.05 R, 2.05 D, 128/2.05 F, 214.4, 348–351

[56] References Cited

U.S. PATENT DOCUMENTS

| 3,055,361 | 9/1962 | Ballard | 128/214.4 |
|---|---|---|---|
| 3,359,974 | 12/1967 | Khalil | 128/2.05 F |
| 3,437,088 | 4/1969 | Bielinski | 128/348 X |
| 3,885,567 | 5/1975 | Ross | 128/240 |
| 3,995,623 | 12/1976 | Blake et al. | 128/349 R X |

FOREIGN PATENT DOCUMENTS 960,932  1/1975  Canada ................... 128/348

Primary Examiner—Dalton L. Truluck
Attorney, Agent, or Firm—Finnegan, Henderson, Farabow & Garrett

[57] ABSTRACT

A venous catheter device including a plurality of independent and noncommunicating fluid conveying lumens housed within or formed in a single catheter. One end of each lumen is adapted to be connected to a different fluid source, such as an intravenous (IV) drug infusion or feeder device, a syringe, etc., or to a central venous pressure (CVP) measuring device. The other end of each lumen exits at or proximate to the catheter terminus which, in turn, is adapted to be positioned within a vein. A hollow needle slidably receives the catheter terminus and is adapted for vein penetration and catheter positioning within the penetrated vein. Alternatively, the catheter can be used without a needle in which case a vein is directly exposed and partially transected allowing direct insertion of the catheter.

10 Claims, 6 Drawing Figures

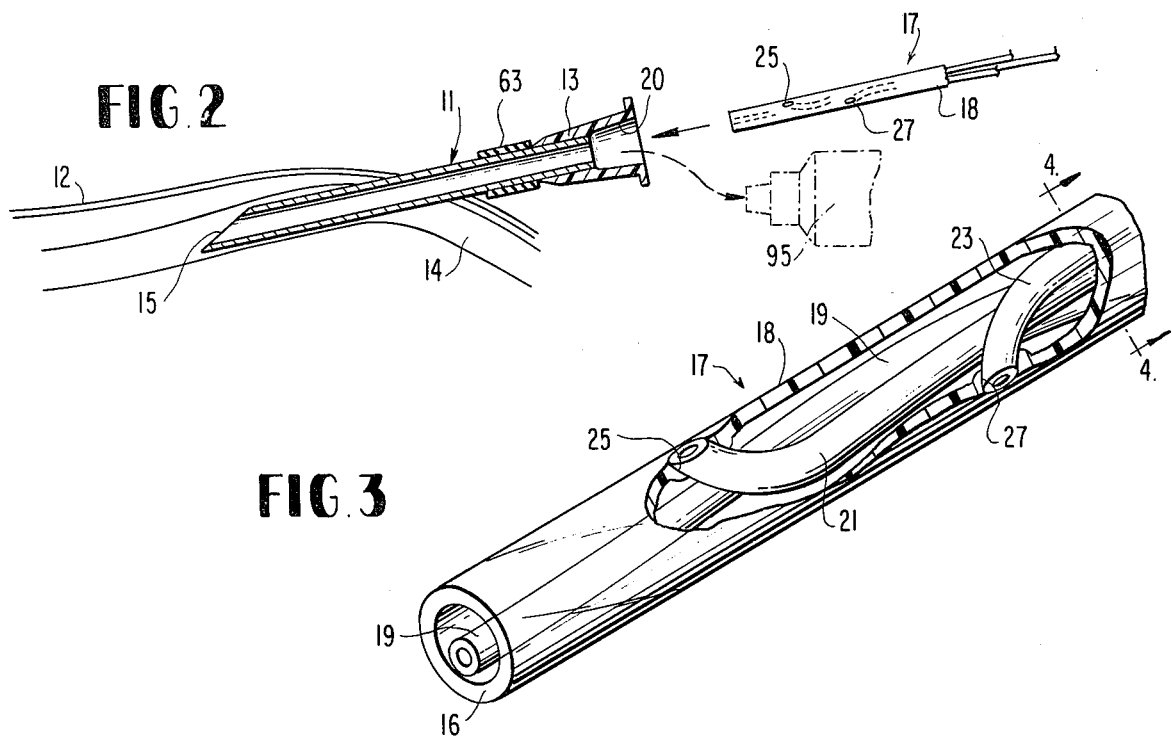
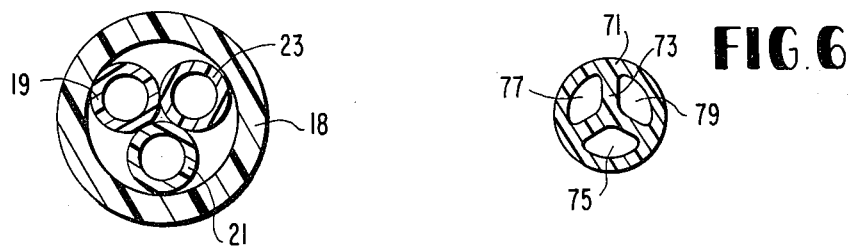
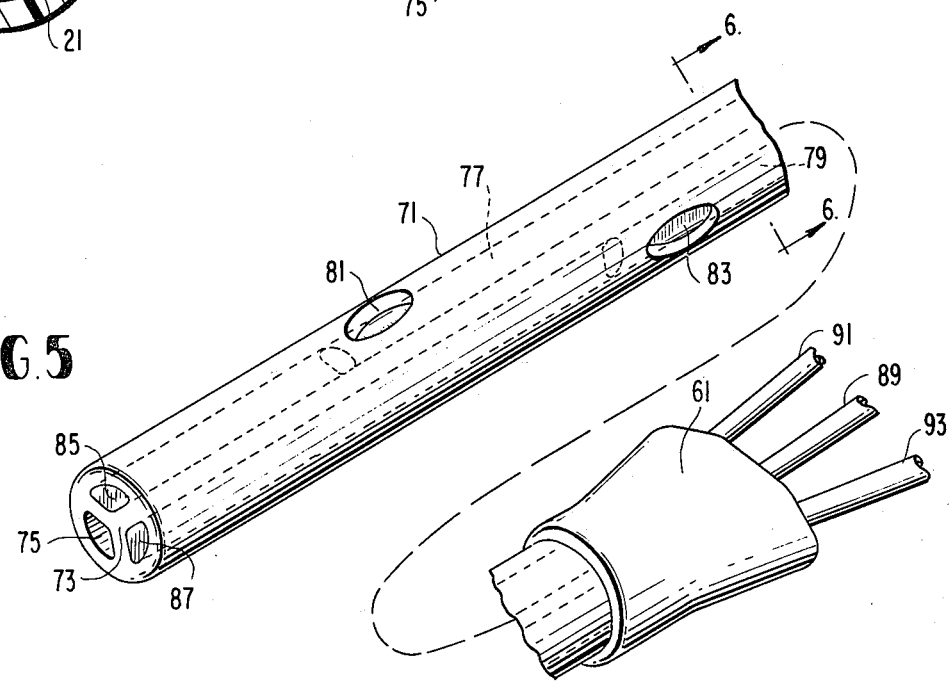

VENOUS CATHETER DEVICE

This invention relates to venous catheter devices, more particularly, this invention relates to a single catheter device that may be used to infuse multiple fluids, including nourishment and drugs, crystalloids, colloids, and blood and/or blood products, simultaneously into a patient's vein. In addition, the catheter of the present invention may be used for central venous pressure (CVP) monitoring and/or removal of blood samples simultaneously with drug and/or fluid infusion.

Conventional venous catheter devices utilize a single lumen, and each is used singly to achieve one of the following: administer one drug or IV feeding; monitor central venous pressure (CVP); or withdrawing blood samples. Only one drug or IV fluid can be administered through a single lumen catheter since it is undesirable and contraindicated to mix many of these drugs and IV fluids prior to their entering the bloodstream. Furthermore, CVP monitoring and withdrawal of a blood sample cannot be performed simultaneously with drug or fluid infusion using a single lumen catheter. Also, a single lumen catheter should not be used to alternately administer different drugs and fluids, monitor CVP, and take blood samples, because of the mixing problems described above, and because the catheter can clot and become inoperative.

Many patients, especially those in intensive care units, require simultaneous drug administration, IV feeding, CVP monitoring, and periodic blood sampling. In the past, this has meant that such patients require insertion of a corresponding number of catheter devices simultaneously coupled to major veins such as the external or internal jugular, subclavian, cephalic, femoral or saphenous veins. Obviously, this necessitates considerable patient risk and is a source of great discomfort, possible bleeding, and possible infection to a patient. Furthermore, since it is necessary to move the location of these catheters periodically, e.g., every three or four days, each location requires performing a new puncture (or vein exposure and partial transection), patient discomfort and the chance of infection or complication increases accordingly.

In an effort to minimize the discomfort, complication, and infection problems described above, it has been proposed to use catheters having multiple branched lumens merging in "Y" fashion in a single lumen. In these devices, a single insertion can serve to infuse several fluids into a patient's vein, withdraw blood samples, and monitor vein pressure. However, of these prior art patented devices, those suggesting simultaneous drug or fluid administration suffer the above described drawback of drug and fluid mixing prior to entering the bloodstream. In fact, some of the prior art patents recognized this problem and tried to minimize it by minimizing the length of the single lumen joining the branches and the needle. While this may reduce the problem of drug or fluid mixing before entering the bloodstream, it does not eliminate it.

Furthermore, of these prior art patented devices, those contemplating fluid infusion, blood sampling, and pressure monitoring perform these functions alternately such that it is necessary to seal off all but the one lumen in use. Thus, it is not possible to have simultaneous infusion, CVP monitoring, and blood sampling with these devices.

It is apparent, therefore, that a single venous catheter device capable of simultaneously infusing several fluids, monitoring CVP, and/or taking blood samples, and which overcomes the problem of fluid mixing before entering the bloodstream, is highly desirable.

Accordingly, it is a primary object of this invention to provide an improved venous catheter device.

It is a further object of this invention to provide an improved venous catheter device adapted to infuse a plurality of fluids into a patient's vein simultaneously and without mixing the fluids, medications, and/or blood products before entering the bloodstream.

A further object of this invention is to provide an improved venous catheter device which may be used to monitor venous pressure simultaneously with fluid infusion, and which may be used to withdraw blood samples from the patient's vein simultaneously with either or both of the above.

Another object of the present invention is to provide an improved venous catheter device which minimizes patient discomfort and decreases the possibility of associated complications such as infection and bleeding.

Still another object of this invention is to provide an improved venous catheter device embodying multiple lumens adapted for multiple and simultaneous operations as described, wherein means is provided identifying individual lumens for preferred functions in use.

Still another object of the present invention is to provide a new multi-lumened venous catheter device wherein each lumen is provided with an adapter facilitating ready connection to individual fluid sources.

Other objects of the present invention are to provide an improved venous catheter device which may be used together with a needle as a venipuncture device, or apart from a needle in which case a vein is exposed and partially transected and the catheter directly inserted.

Still other objects of the present invention are to provide an improved venous catheter device which is relatively inexpensive to manufacture, readily sterilizable, sturdy in construction, and reliable and efficient in use.

Additional objects and advantages of the present invention will become more apparent from a consideration of the detailed description which follows, and in part will be obvious from this description or may be learned by practice of this invention. The objects and advantages of this invention may be realized and attained by means of the instrumentalities and combinations particularly pointed out in the appended claims.

To achieve the foregoing objects and in accordance with the purpose of the invention, as embodied and broadly described herein, the venous catheter device of this invention comprises an elongated flexible catheter having a plurality of independent and non-communicating fluid conveying lumens extending therethrough, said lumens having their terminii spaced from one another and exiting from said catheter near its terminus, the other end of each of said lumens being adapted for connection to a separate fluid source such as an intravenous bottle or a syringe, or to a pressure monitoring device, whereby a plurality of fluids may be infused into a patient's vein, the patient's CVP may be monitored, and blood samples can be withdrawn, all simultaneously or selectively.

The venous catheter device of this invention can be used together with a venipuncture needle in which case the needle is hollow and slidably receives the terminus of the catheter. Alternatively, the catheter device can be used apart from a needle wherein the catheter is directly inserted into an exposed and partially transected vein.

In addition, each lumen is provided with a lumen adapter, and the lumens or the adapters may be appropriately marked or color coded to suggest a preferred use for the individual lumens.

Furthermore, each lumen is constructed so that it can adapt to a control valve and/or a flow plug so that each lumen may be selectively and individually closed off when not in use, but may be readily opened up when use is desired.

OF THE DRAWINGS

FIG. 2 is an enlarged view, partly in section, showing a venipuncture needle in position in a vein and the catheter of this invention about to be inserted through the needle into the vein;

FIG. 3 is an enlarged view, partly in section, of a portion of FIG. 1 showing the catheter terminus and the multiple lumens;

FIG. 4 is an enlarged sectional view of FIG. 3 taken along the line 4—4 thereof;

FIG. 5 is a view similar to FIG. 3 but showing a modified form of the invention; and FIG. 6 is a sectional view of FIG. 5 taken along the line 6—6 thereof.

Figure 1:
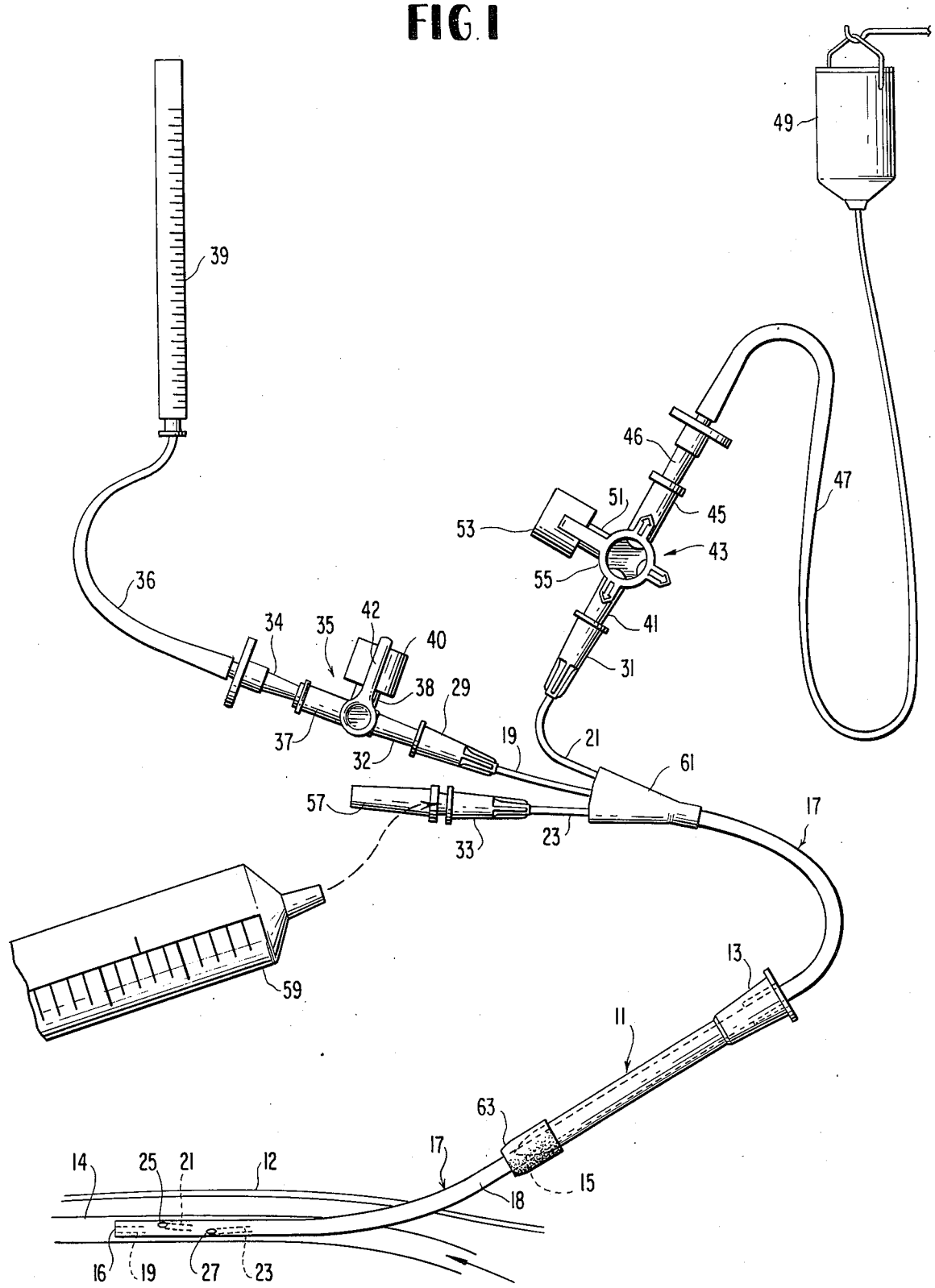
FIG. 1 is a view illustrating a three lumen catheter constructed in accordance with a preferred form of the invention and shown with the catheter in position in a vein and with a venipuncture needle withdrawn and protected and showing the catheter connected to a variety of fluid sources.

As used herein "lumen" is intended to mean fluid conduit means and may include individual tubes, or elongated openings or passages formed in a body, or it may include individual tubes connected to elongated passages in a body.

Referring now to the drawings, a venous catheter device constructed in accordance with the present invention is shown associated with a hollow needle 11 supported at one end by a hollow needle hub 13 of Luer Lok[1] design for connection to a variety of syringe tips. The other end of the needle 11 is formed with a sharpened and tapered tip 15 for penetrating the skin 12 and a vein 14 of a patient.

[1] Trademark of Becton, Dickinson and Company, Rutherford, N.J.

In accordance with the invention, an elongated flexible catheter 17 is provided and is adapted to extend through an opening 20 in the hub 13 and through the hollow needle 11, and beyond the needle tip 15 when positioned in a vein. The catheter 17 is slightly smaller in outer diameter than the inner diameter of the needle 11 so as to slidably fit through the needle.

In accordance with a preferred form of the invention, the catheter 17 includes an outer tube 18 with a plurality of lumens positioned therein and extending longitudinally therethrough. The lumens, being illustrated as three in number and identified as 19, 21, 23, are totally independent from and not communicative with one another, and each extends to a point proximate the terminus 16 of the catheter tube 18. As shown, lumen 19 terminates substantially coextensive with the catheter terminus 16. Lumens 21, 23 terminate at openings 25, 27 in the side of catheter tube 18 at points axially spaced from one another and from the terminus of lumen 19. Preferably, the terminus of lumens 19, 21, 23 are spaced at least about one centimeter apart longitudinally of the catheter tube 18, although this distance could be as much as three centimeters or more. The lumens 19, 21, 23 and tube 18 are formed of a suitable, flexible, heat sterilizable material such as is used in single lumen catheters, and the lumens 21, 23 preferably are joined to the tube 18 at openings 25, 27 using an adhesive, or by fusing.

In accordance with this preferred form of the invention, the proximate ends of lumens 19, 21, 23 extend beyond the proximate end of the catheter tube 18, and each is provided with an adapter 29, 31, 33, respectively, for attachment to a suitable device or fluid source. Adapter 29 is shown receiving one leg 32 of a flow control valve 35 which may, in turn, have another leg 37 receiving a fitting 34 fixed to one end of a conduit 36 for a central venous pressure (CVP) measuring device 39. Still another leg 38 of valve 35 may be connected to another fluid source or device (not shown) which may be alternately communicated with leg 32 and lumen 19. As shown, leg 38 is closed off by a cap 40. A control lever 42 of valve 35 is turnable to open and close communication between the valve legs 37, 38 and valve leg 32. In the position shown, the valve legs 32, 37 are communicated and CVP device 39 is operative.

Adapter 31 is shown receiving one leg 41 of stopcock valve 43. Another leg 45 of valve 43 receives a fitting 46 fixed to conduit 47 connected to an IV bottle 49. A third leg 51 of valve 43 is shown closed off by a cap 53. A control knob 55 on valve 43 selectively communicates leg 41 with leg 45 or leg 51, or both. In the position shown, legs 41, 45 are communicated so that fluid from IV bottle is flowing into lumen 21.

Finally, adapter 33 has a flow plug 57 fitted therein to seal off lumen 23. However, this plug can be removed and adapter 33 fitted with a syringe 59 for infusing drugs or taking blood samples.

In accordance with the invention, lumens 19, 21, 23 are totally independent of and non-communicative with one another so that fluids carried thereby will not mix prior to entering the bloodstream. In addition, and as described, lumens 19, 21, 23 can be used simultaneously for CVP monitoring, fluid infusion, and drug injection and blood sampling. To achieve this, the terminus of each lumen, namely the terminus 16 of catheter tube 18, and openings 25, 27 in the catheter tube 18, are axially spaced from each other by a distance of at least about one centimeter and up to about three centimeters or more. Thus, when the catheter 17 is so positioned in a vein, two or more fluids can be infused simultaneously into the bloodstream using any of the lumens 19, 21, 23 without mixing prior to entry. The spacing of at least one centimeter between lumen terminii is sufficient to prevent any mixing problem.

Furthermore, this individuality of the lumens allows a patient's CVP to be monitored, and, if desired, blood samples to be taken, at the same time fluids are being administered, and all of this is achieved with one vein puncture if a needle 11 is used, or one vein exposure and partial transection if a needle 11 is not used. Prior to the present invention, it was necessary to make one puncture (or partial transection) for each fluid infusion, pressure measurement, and blood sampling procedure to be performed on a patient simultaneously. Thus, where several, e.g., three or more punctures (or partial transections) were required previously, only one is required with the present invention. This results in a considerable reduction in risk and discomfort to the patient and obviously reduces the likelihood of subsequent infection and complication.

These advantages are, of course, amplified by the fact that venous catheters must be moved periodically, for example, every three or four days. Thus, while several new punctures (or partial transections) were previously required approximately every three or four days, now only one is required. The reduction in risk and discomfort to a patient, and the reduction in the likelihood of subsequent complication, infection or inflammation caused by these punctures is immeasurable.

In accordance with another feature of this invention, the several lumen adapters 29, 31, 33 may be color coded or otherwise identified to suggest particular usage for the lumens associated therewith. For example, CVP measurement will best be provided using lumen 19 which exits centrally of the catheter tube 18 since that lumen cannot contact the vein wall which otherwise might distort pressure readings obtained. Lumen 23 is best adapted for withdrawal of blood samples from a patient's vein since its terminus 27 is furthest upstream in the direction of blood flow. Thus, any drugs or IV feedings delivered through lumens 19 or 21 will be downstream of terminus 27 and the sample of blood withdrawn through terminus 27 and lumen 23 is pure. Of course, it will be understood that all lumens 19, 21, and 23 are available for IV or medicinal injections, and that any of the lumens can be used for CVP monitoring. The coding of adapters 29, 31, 33 can be any suitable means, such as coloring, letters or numbers, and the instructions accompanying the catheter can inform the catheter user of the intended and recommended usage thereof.

The preferred embodiment illustrated and described herein is shown with three lumens encased within a single catheter tube. It is clear that the number of lumens may be varied, and it should be understood that the inventive concept herein resides in the use of a plurality of fluid conveying lumens disposed in a single catheter, the lumens being separate and independent from one another and non-communicative, and that the terminus of the lumens are adjacent to the catheter terminus but are axially spaced from one another. The lumens shown and described are encased in a separate catheter tube and each lumen has its terminus suitably joined or fused to the respective terminus openings adjacent the catheter tube end.

It will be understood that a number of manufacturing techniques can be employed to form this catheter-lumen assembly, and that arrangements other than that shown herein can be employed, it being understood that the catheter-lumen assembly be constructed preferably from a suitable heat sterilizable material. For example, the catheter and lumens can be integrally formed such that the lumens are elongated openings through the catheter body itself, rather than the lumens being separate tubes confined within a separate catheter sheath. Such an arrangement is shown in FIGS. 5 and 6, the catheter being depicted as having an outer sheath 71 and an inner walled portion 73 dividing the catheter into separate lumens 75, 77, 79 extending therethrough. The sheath 71 and walled portion 73 can be integrally formed, or separately formed and suitably joined. In this embodiment, lumen 75 extends to the catheter terminus, while lumens 77, 79 exit through openings 81, 83 each spaced at least one centimeter from the terminus and from each other. The lumens 77, 74 forwardly of openings 81, 83 are shown blocked by plugs 85, 87, respectively.

In the embodiment of FIGS. 5 and 6, separate lumens 89, 91, 93 have their distal ends positioned in and suitably fixed to lumens 75, 77, 79, respectively, and have their proximate ends extending from the catheter body. This is similar to the embodiment of FIGS. 1-3 where the proximate ends of lumens 19, 21, 23 also extend from catheter body 17. In both embodiments, proximate ends of the lumens desirably are provided with the separate catheter adapters as shown. Preferably, the lumens are suitably joined in both embodiments by a Y-connector 61, as shown, at the area where they emerge from the catheter tube 18 (or 71) for convenience in handling and for strength. This Y-connector can be suitably molded using known techniques, and serves to prevent the lumens from being pulled apart in use.

Furthermore, it will be understood that one or more of the lumens can be closed off during use of the catheter by using a flow control plug 57 or one of the valves 35, 43 described above. However, should it become necessary to use a closed-off lumen, it is a simple matter to remove this flow control plug 57 or open the valve 35, 43 and then attach a suitable fluid device (IV bottle, syringe, etc.) while the catheter is in place within a patient's vein. Conversely, with the catheter in place, any one or more of the lumens can be closed off by reversing the above procedure.

The manner of using the venous catheter of the present invention is substantially the same as a single lumen venous catheter. Thus, if the venous catheter is used with needle 11, the catheter tube 18 is initially withdrawn within the needle 11. A venipuncture is then made using the needle 11 to position the end 15 of the needle 11 in place within a patient's vein. Thereafter, the catheter 17 is slid longitudinally through the needle 11 so as to extend beyond the needle tip 15 and into the punctured vein. While holding the catheter tube 18, the needle 11 is withdrawn from the vein. A needle guard 63 constructed of a flexible plastic, heat sterilizable material frictionally grips the needle 11 and is slid along the needle 11 and positioned over the needle tip 15 to prevent it from severing the catheter tube 18. The assembly is then suitably attached, as by tape or suture, to the patient adjacent to the puncture in the usual fashion. The catheter is then in place and the desired lumens are ready for attachment to suitable fluid conveying devices, CVP measuring devices, etc.

Alternatively, a venipuncture can be made using needle 11 and a connected syringe 95 (FIG. 2) and with the catheter 17 completely withdrawn from the needle 11. With the needle 11 held in position in vein 14, the syringe 95 is detached and the catheter 17 fed through needle hub 13 and needle 11 into vein 14. Holding catheter, needle 11 is then withdrawn, guard 63 is slid into position over needle tip 15, and the assembly attached to the patient as described above.

When used without a needle, a venous "cut-down" is first made in which the desired vein (either the saphenous, cephalic, anticubital and/or the external jugular) is directly exposed and partially transected. The catheter is then directly inserted into the vein without using a needle and is attached by tape or suture.

The present invention provides a venous catheter device that is usable for infusion of more than one fluid simultaneously into the vein of a patient. Also, blood samples may be withdrawn and CVP measurements may be taken simultaneously with fluid infusion, and with but a single puncture of the patient's vein.

It will be apparent to those skilled in the art that various additions, modifications, substitutions and omissions may be made in the catheter of the present invention without departing from the scope or spirit of the invention.

What is claimed is:

1. A venipuncture device including a hollow needle having a generally circular cross-section, an elongated, flexible catheter provided with a distal end portion generally circular in cross-section and having a uniform outer diameter slidably extending through said needle and capable of being fed longitudinally into a vein, a plurality of fluid passages extending longitudinally of said catheter and each having a terminus at the distal end portion of said catheter and defining an opening to the outside of said catheter, the terminus of each of said passages being spaced from one another by a distance of at least about one centimeter, said fluid passages being defined at least in part by elongated flexible lumens extending from the proximate end of said catheter, each of said lumens being adapted for attachment to a separate fluid conveying device, whereby fluids may be separately infused into the vein of a patent without becoming mixed before infusion, and whereby blood samples may be withdrawn and venous pressure measurements performed simultaneously with fluid infusion.

2. A venipuncture device including a hollow needle having a generally circular cross-section, an elongated, flexible catheter provided with a distal end portion generally circular in cross-section and having a uniform outer diameter slidably extending through said needle and capable of being fed longitudinally into a vein, said catheter including an elongated tube and having a plurality of independent lumens extending longitudinally thereof, one of said lumens terminating substantially coextensive with the catheter tube terminus at the distal end portion, the other of said lumens terminating at the distal end portion of said catheter and defining an opening to the outside of said catheter tube, each of said lumens having its terminus spaced from each of the other lumen termini by a distance of at least about one centimeter, each of said lumens having its proximate end remote from said catheter distal end portion extending beyond said catheter tube and fitted with a lumen adapter, whereby each of said lumens may be connected to a fluid flow device and may be simultaneously used to infuse fluid into the vein of a patient, to withdraw blood samples from the patient's vein and to take venous pressure measurements simultaneously with said fluid infusion and blood sample withdrawal.

3. A venipuncture device including a hollow needle having a generally circular cross-section, an elongated, flexible catheter tube provided with a distal end portion generally circular in cross-section and having a uniform outer diameter slidably extending through said needle and capable of being fed longitudinally into a vein, a plurality of independent lumens extending through said catheter tube, each of said lumens having a terminus at the distal end portion of said catheter and defining an opening to the outside of the catheter tube and being spaced from each other, the proximate ends of the lumens remote from the catheter distal terminus extending beyond said catheter tube and being fitted with a lumen adapter for connection to independent fluid devices, each of said lumen adapters being provided with indicia to indicate a corresponding lumen to which the adapter is connected and the position of each lumen terminus relative to the terminus of said catheter tube.

4. A venipuncture device including a hollow elongated needle having a generally circular cross-section, an elongated, flexible catheter tube provided with a distal end portion generally circular in cross-section and having a uniform outer diameter slidably extending through said needle and capable of being fed longitudinally into a vein, a plurality of elongated, flexible lumens encased within said catheter tube and each having a distal terminus adjacent the distal end portion of said catheter, and a proximate end extending beyond the proximate end of said catheter, the distal terminus of one of said lumens being substantially coextensive with the distal terminus of the catheter tube and the distal termini of the other lumens each extending through a separate side opening in said catheter tube, all of said lumen termini being spaced from each of the other lumen termini by a distance of at least about one centimeter, a connector molded over the proximate end of said catheter tube and encasing a portion of the individual lumens extending beyond the proximate end of the catheter tube, each of said lumens having a lumen adapter fitted on its proximate end, whereby to facilitate connection of the individual lumens to separate fluid devices, said adapters being formed to receive flexible conduits and flow control valves for controlling flow of fluid in the individual lumens.

5. A venous catheter device including an elongated, integral flexible catheter tube provided with a distal end portion generally circular in cross-section and having a uniform outer diameter constructed for insertion into and capable of being fed longitudinally of a vein, a plurality of independent lumens extending through said catheter tube, each of said lumens having a distal terminus adjacent the distal terminus of the catheter tube and defining an opening to the outside of said catheter tube, the distal terminus of said lumens being spaced from each other and all of said lumen termini being within no more than about twelve centimeters from the distal terminus of the catheter tube, the proximate ends of the lumens extending beyond the proximate end of said catheter tube and being fitted with a lumen adapter for connection to independent fluid devices.

6. A venous catheter device including an elongated, flexible catheter provided with a distal end portion generally circular in cross-section and having a uniform outer diameter constructed for insertion into and capable of being fed longitudinally of a vein, a plurality of fluid passages extending longitudinally of said catheter and each having a terminus at the distal end portion of said catheter and defining an opening to the outside of said catheter, the terminus of each of said passages being spaced from one another by a distance of at least about one centimeter, said fluid passages being defined at least in part by elongated flexible lumens extending from the proximate end of said catheter, remote from said terminus, at least one of said passages providing means for infusing fluids into the blood stream, and each of said lumens being adapted for attachment to a separate fluid conveying device, whereby fluids may be separately infused into the vein of a patient without becoming mixed before infusion, and whereby blood samples may be withdrawn and venous pressure measurements performed simultaneously with fluid infusion.

7. A venous catheter device including an elongated, flexible catheter tube provided with a distal end portion generally circular in cross-section and having a uniform outer diameter constructed for insertion into and capable of being fed longitudinally of a vein, a plurality of independent lumens extending freely through said catheter tube, each of said lumens having a distal terminus adjacent the distal terminus of the catheter tube and spaced from each other, one of said lumens having its distal end substantially coextensive with the distal end of said tube, the other of said lumens exiting at lateral openings in said tube and being joined thereto, at least one of said lumens providing means for infusing fluids into the blood stream, the proximate ends of the lumens extending beyond the proximate end of said catheter tube and being fitted with a lumen adapter for connection to independent fluid devices.

8. A venous catheter device including an elongated, integral flexible catheter tube provided with a distal end portion generally circular in cross-section and having a uniform outer diameter constructed for insertion into and capable of being fed longitudinally of a vein, a plurality of lumens formed as passages in said tube and extending through said catheter tube, each of said lumens having a distal terminus at the distal end portion of the catheter tube and defining an opening to the outside of said catheter tube and being spaced from each other, the proximate ends of the lumens extending beyond the proximate end of said catheter tube and being fitted with a lumen adpater for connection to independent fluid devices, at least one of said lumens providing means for infusing fluids into the blood stream.

9. A venipuncture device including a hollow needle having a generally circular cross-section, an elongated, flexible catheter provided with a distal end portion generally circular in cross-section and having a uniform outer diameter slidably extended through said needle and capable of being fed longitudinally into a vein, a plurality of fluid passages extending longitudinally of said catheter and each having a terminus at the distal end portion of said catheter and defining an opening to the outside of said catheter, the terminus of each of said passages being spaced from one another by a distance of at least about one centimeter, each of said passages being adapted for attachment to a separate fluid conveying device, whereby fluids may be separately infused into the vein of a patient without becoming mixed before infusion, and whereby blood samples may be withdrawn and venous pressure measurements performed simultaneously with fluid infusion.

10. A venous catheter device including an elongated, flexible catheter provided with a distal end portion generally circular in cross-section and having a uniform outer diameter constructed for insertion into or capable of being fed longitudinally into a vein, a plurality of fluid passages extending longitudinally of said catheter and defining an opening to the outside of said catheter, the terminus of each of said passages being spaced from one another by a distance of at least about one centimeter, each of the passages providing means for selectively infusing fluids into the blood stream, withdrawing blood samples, and measuring venous pressure, each of said passages being adapted for attachment to a separate fluid conveying device, whereby fluids may be separately infused into a vein of a patient without becoming mixed before infusion, and whereby blood samples may be withdrawn and venous pressure measurements performed simultaneously with fluid infusion.

* * * * *